US009606080B2

United States Patent
Thekkedath et al.

(10) Patent No.: US 9,606,080 B2
(45) Date of Patent: Mar. 28, 2017

(54) NON-ENZYMATIC GLUCOSE SENSOR

(71) Applicants: Satheesh Babu G. Thekkedath, The Nilgiris (IN); Ramachandran Thiagarajan, Coimbatore (IN); Bipin G. Nair, Kollam (IN)

(72) Inventors: Satheesh Babu G. Thekkedath, The Nilgiris (IN); Ramachandran Thiagarajan, Coimbatore (IN); Bipin G. Nair, Kollam (IN)

(73) Assignee: Amrita Vishwa Vidyapeetham, Amritaprui, Kollam, Kerala (IN)

( * ) Notice: Subject to any disclaimer, the term of this patent is extended or adjusted under 35 U.S.C. 154(b) by 232 days.

(21) Appl. No.: 14/019,314

(22) Filed: Sep. 5, 2013

(65) Prior Publication Data
US 2014/0061044 A1 Mar. 6, 2014

(30) Foreign Application Priority Data

Sep. 6, 2012 (IN) .............................. 3697/CHE/2012

(51) Int. Cl.
*G01N 27/327* (2006.01)
(52) U.S. Cl.
CPC ................................ *G01N 27/3278* (2013.01)
(58) Field of Classification Search
CPC ..................................... G01N 27/327–27/3272
See application file for complete search history.

(56) References Cited

U.S. PATENT DOCUMENTS

| 4,250,398 A * | 2/1981 | Ellis .......................... B32B 7/02 219/528 |
| 6,471,839 B1 * | 10/2002 | Yamamoto .............. C12Q 1/004 204/403.06 |
| 7,112,265 B1 * | 9/2006 | McAleer ............ G01N 27/3272 204/403.05 |
| 7,419,580 B2 | 9/2008 | Chan et al. |
| 2007/0034512 A1 | 2/2007 | Yamaoka et al. |
| 2009/0071538 A1 * | 3/2009 | Lee et al. ........................ 136/257 |
| 2010/0200538 A1 | 8/2010 | Petisce et al. |
| 2011/0046466 A1 | 2/2011 | Feldman et al. |
| 2011/0129593 A1 | 6/2011 | Lee et al. |

FOREIGN PATENT DOCUMENTS

| WO | 2012018777 A1 | 2/2012 |
| WO | WO 2012/018777 | * 2/2012 |

OTHER PUBLICATIONS

Yang et al. (Talanta 82 (2010) 25-33).*
Luo et al. (Talanta 86 (2011) 157-163).*
Cao et al. (Analytica Chimica Acta 723, 2012, 39-44).*
You et al. (Electrochemistry Communications 4 (2002) 468-471).*
(Continued)

*Primary Examiner* — Alexander Noguerola
(74) *Attorney, Agent, or Firm* — Convergence Intellectual Property Law P.C.; Jonathan Garfinkel

(57) ABSTRACT

A non-enzymatic glucose sensor and method for fabricating the sensor are disclosed. The glucose sensor contains at least one non-enzymatic electrode configured to catalyze the electro-oxidation of glucose in preference to other biomolecules. The surface of the electrode comprises CuO nanoparticles. The sensor shows sensitivity and selectivity exceeding enzyme based devices presently in use.

4 Claims, 8 Drawing Sheets

(56) References Cited

OTHER PUBLICATIONS

Lanje et al. (Advances in Applied Science Research, 2010, 1 (2): 36-40).*
Wang et al. (Sensors and Actuators B 144 (2010) 220-225).*
Xu et al. (Sensors and Actuators B 114 (2006) 379-386).*
Chuan Jiang et al. (Biosensors and Bioelectronics 25 (2010) 1402-1407).*
Wang et al. (Letters, 10, 2007).*
Zhang et al. (Sensors and Actuators B 191 (2014) 86-93).*
Reitz et al. (Electroanalysis 20, 2008, No. 22, 2482-2486).*
Zhang X., et al., "Fixure-Reduce Method for the Synthesis of Cu2O/MWCNTs Nanocomposites and Its Application as Enzyme-Free Glucose Sensor," Biosensors and Bioelectronics, 2009, vol. 24 (1), pp. 3395-3398.

\* cited by examiner

NON-ENZYMATIC GLUCOSE SENSOR

RELATED APPLICATION

The present application claims priority under 35 U.S.C. §119 to Indian Patent Application No. 3697/CHE/2012, filed Sep. 6, 2012, the full disclosure of which is incorporated herein by reference.

BACKGROUND

The present disclosure relates generally to glucose sensors. In particular, the present disclosure relates to non-enzymatic glucose sensors and methods for fabricating the same.

Diabetes mellitus is a metabolic disorder that results from insulin deficiency and is reflected by blood glucose concentrations being outside the normal range of 80-120 mg/dL. Diabetes causes complications such as neuropathy, nephropathy and retinopathy which result in heart disease, kidney failure, or blindness, respectively. Therefore, in order to treat diabetes, it is very important for diabetics to control their blood glucose levels by conducting self-monitoring several times a day. A wide variety of methods for glucose analysis, including electrochemistry, near infrared spectroscopy, optical rotation and the like, have been reported in the literature.

The most commonly used technology for blood glucose determination is an enzyme based method. The enzymatic glucose sensors have a serious drawback of oxygen dependence. The errors emanating from this high dependence on oxygen to mediate regeneration of the catalytic center are quite significant as oxygen levels in blood vary considerably. Often enough oxygen is not available in a real blood sample to efficiently maintain glucose oxidation, thus this oxygen deficit has a great impact on accurate determination of glucose levels. The enzyme based glucose sensors also encounter problems in terms of the stability of the enzyme, the role of the mediator, enzyme leaching etc.

Though enzymatic glucose sensors are extensively studied and applied, one problem with these sensors is their short shelf life, which originates from the intrinsic nature of the enzymes. Further, a complicated procedure, including processes such as adsorption, cross-linking, entrapment, and electropolymerization, is required for the immobilization of the enzyme on the solid electrode, and this may decrease the activity of the Glucose oxidase. Since the sensitivity of these glucose sensors essentially depends on the activity of the immobilized enzymes, reproducibility is still a critical issue in quality control.

To overcome the above mentioned problems associated with the enzymatic glucose sensors, the use of alternative co-substrates emerged. Synthetic, electron-accepting mediators are utilized to facilitate electron transfer and their subsequent re-oxidation on the electrode resulting in a quantifiable amperometric current. A number of non-physiological mediators have been reported including ferrocene derivatives and ferricyanide of which most commercial sensors use quinines and transition-metal complexes. Several problems still remain when using a mediator. Maintaining the mediator molecules, which are small and diffusive in nature, near the electrode and on the enzyme surface is very difficult, particularly over prolonged use and that creates a need for elaborate and complicated methods of tethering the mediator to the two entities. Although the mediator ideally reacts with the enzyme at a considerably faster rate than oxygen, the possibility of dissolved oxygen also competing with the mediator is highly likely, thus reducing the efficiency of the system and causing a buildup of hydrogen peroxide. It is also possible for the mediator to react with interfering species present in the blood, further affecting the accuracy and efficiency of the analytical system.

Three essential requirements for a material having good sensor characteristics are sensitivity, selectivity and mechanical stability. Components chosen for the fabrication of the sensor electrode should satisfy these three requirements. Furthermore, the sensor electrode fabrication processes should be reproducible and able to be applied for commercial purposes in a simple manner.

Therefore there is a need for glucose sensing technology having sensors with high degree of selectivity and sensitivity and stable at wide range of temperature/humidity, as proposed herein.

RELATED ART

U.S. Publication No. 20110046466 titled "Analyte sensors including nanomaterials and methods of using the same" by Feldman, et al., filed Aug. 19, 2009; U.S. Publication No. 20070034512 titled "Biosensor and method for producing the same" by Yamaoka et al., filed Oct. 29, 2004; U.S. Publication No. 20110129593 titled "Composition for glucose sensing comprising of nanofibrous membrane and method for manufacturing non-enzymatic glucose biosensor using the same" by Lee et al., filed Oct. 24, 2008; U.S. Publication No. 20100200538 titled "Analyte sensors and fabrication methods" by Petisce et al., filed Feb. 3, 2010; U.S. Pat. No. 7,419,580, titled "Methods and apparatus for oxidation of glucose molecules" by Chan et al., filed Nov. 28, 2001. WO2012018777 to Yu et al. entitled "Non-enzymatic glucose sensors based on metal oxide nanomaterials" discloses mixed oxide nanofiber compositions containing oxides of nickel, copper and cobalt for glucose sensing, while Zhang et al. (Biosensors and Bioelectronics 24 (2009) 3395-3398) proposes a sensor with $Cu_2O$ nanoparticles loaded within multi-walled carbon nanotubes.

SUMMARY

Systems, devices, and methods for detecting glucose and method for fabricating glucose sensors are disclosed.

In one aspect, a non-enzymatic glucose sensor comprises an electrode layer with at least one electrode. In one aspect, the electrode is non-enzymatic and is configured to catalyze the electro-oxidation of glucose in preference to other biomolecules. In one aspect, the electrode is fabricated by screen printing technique. In one aspect, the surface of the electrode comprises silver based body coated substantially with conducting carbon ink and copper oxide nanoparticles. The size of the nanoparticles preferably ranges from 5 nm-500 nm. In one aspect, the copper oxide nanoparticles comprises spherical copper oxide nanoparticles which are prepared by annealing copper hydroxide above 400° C. or elongated copper oxide nanoparticles prepared by thermal annealing of copper hydroxide complex at 400° C. for three hours. In another aspect, the copper oxide nanoparticles comprise copper oxide nanowires prepared by annealing copper hydroxide at 180° C. for three hours. The electrodes are connected to a glucometer which senses the glucose level in blood efficiently.

In another aspect, a fabrication method of glucose sensor comprises providing an insulating base plate/substrate on which one or more disposable silver-based electrodes are formed. In one aspect, the insulating base plate/substrate is made up of polyvinylchloride (PVC), polyester (PE), polyether, polycarbonate, or the like. In one aspect, the electrodes are formed on the substrate by screen printing technique. In yet another aspect, the electrodes comprise a working and counter electrodes made up of carbon and a reference electrode made by Ag/AgCl. In one aspect, conductive material such as carbon ink is coated over the silver based electrodes and active materials are deposited onto the electrodes. In one aspect, the active materials are prepared by forming a slurry of copper oxide nanostructures using a solution of sodium hydroxide (NaOH) and isopropyl alcohol at various concentrations and selectively printed onto the electrodes. Then excessive conductive materials and active materials are removed after which suitable openings are defined over the electrodes. In one aspect, the printed electrodes are then dried in a hot air oven at 100° C. for one hour after which the electrodes are stripped off from the substrate. In another aspect, the stripped off electrodes are then incorporated into a flex circuit or medical device for testing the glucose level. In one aspect, the glucose testing strips were tested with glucose solutions of known concentrations, blood and blood serum samples and highly quantitative results were obtained.

This, and further aspects of the present embodiments are set forth herein.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION

Figure 1:
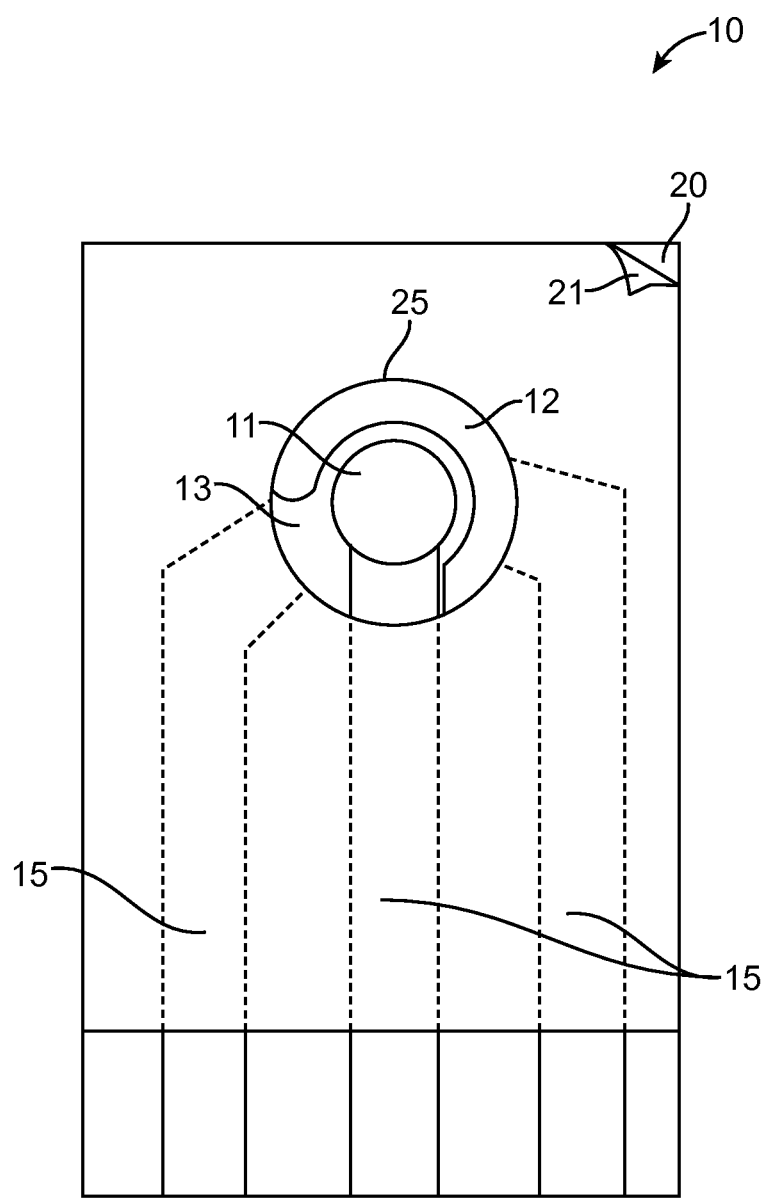
FIG. 1 illustrates one embodiment of a non-enzymatic glucose sensor.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

The present disclosure describes devices, methods, systems, and kits for sensing blood glucose level using glucose sensors and the fabrication of the same. Specifically, the present disclosure contemplates a highly sensitive non-enzymatic glucose sensing device and a method for fabricating the same.

In one embodiment, the glucose sensor comprises one or more disposable glucose sensing strips using nanomaterials and a glucometer for testing. In one embodiment, the sensor is 'enzyme-free' or 'non-enzymatic' in nature thereby avoiding the problems associated with the use of conventional enzymatic sensors such as high cost, short shelf life, complicated immobilization procedure such as adsorption, crosslinking, entrapment, and electropolymerization, etc.

In one aspect, the sensor assembly may be configured for an intravenous insertion to a vascular system of a subject. In order to accommodate the sensor within the confined space of a device suitable for intravenous insertion, the sensor assembly may be assembled onto a flexible circuit. Various devices adaptable to the sensor assembly include, but are not limited to a central venous catheter (CVC), a pulmonary artery catheter (PAC), a probe for insertion through a CVC or PAC or through a peripheral IV catheter, a peripherally inserted catheter (PICC), Swan-Ganz catheter, an introducer or an attachment to a venous arterial blood management protection (VAMP) system. Any sizes or types of central venous catheter (CVC) or intravenous devices may be used or adapted for use with the sensor assembly.

In general, the sensor or the sensor assembly as well as the device that the sensor is adapted to are sterilized before use. In one aspect, the fabrication process includes the sterilization of the sensor. Sterilization may be achieved using aseptic manufacturing, radiation (e.g., electron beam or gamma radiation), ethylene oxide or flash-UV sterilization, or other means known in the art. Disposable portions, if any, of the sensor, sensor assembly or devices adapted to receive and contain the sensor preferably will be sterilized, for example using e-beam or gamma radiation or other known methods. The fully assembled device or any of the disposable components may be packaged inside a sealed container or pouch.

One embodiment of the present disclosure includes a combination of electrode materials that can electrochemically oxidize organic molecules. One embodiment further discloses a combination of electrode materials that can electrochemically oxidize glucose at a very low potential and with a high current density. The low oxidation potential of glucose allows the development of an inorganic glucose sensor with minimum interferences from other dissolved constituents. The use of an inorganic nano-particle as described in the present disclosure will not have the disadvantages noted above for current commercial blood glucose sensors.

Although aspects disclosed herein may be primarily described in the context of glucose sensors used in the treatment of diabetes/diabetic symptoms, the aspects disclosed may be applicable to a wide variety of patient treatment programs where a physiological characteristic is monitored in an ICU, including but not limited to blood gases, pH, temperature and other analytes of interest in the vascular system.

In one embodiment a configuration of the non-enzymatic glucose sensor 10 of the invention is shown in FIG. 1. The glucose sensor comprises at least three electrodes, a working electrode 11, counter electrode 12, and reference electrode 13 disposed on an insulating base/substrate 20. The electrodes are covered by encapsulating layer 21 except in sensing window 25. In one embodiment the active material for the active electrode 11 is a slurry of CuO nanostructures.

Figure 2:
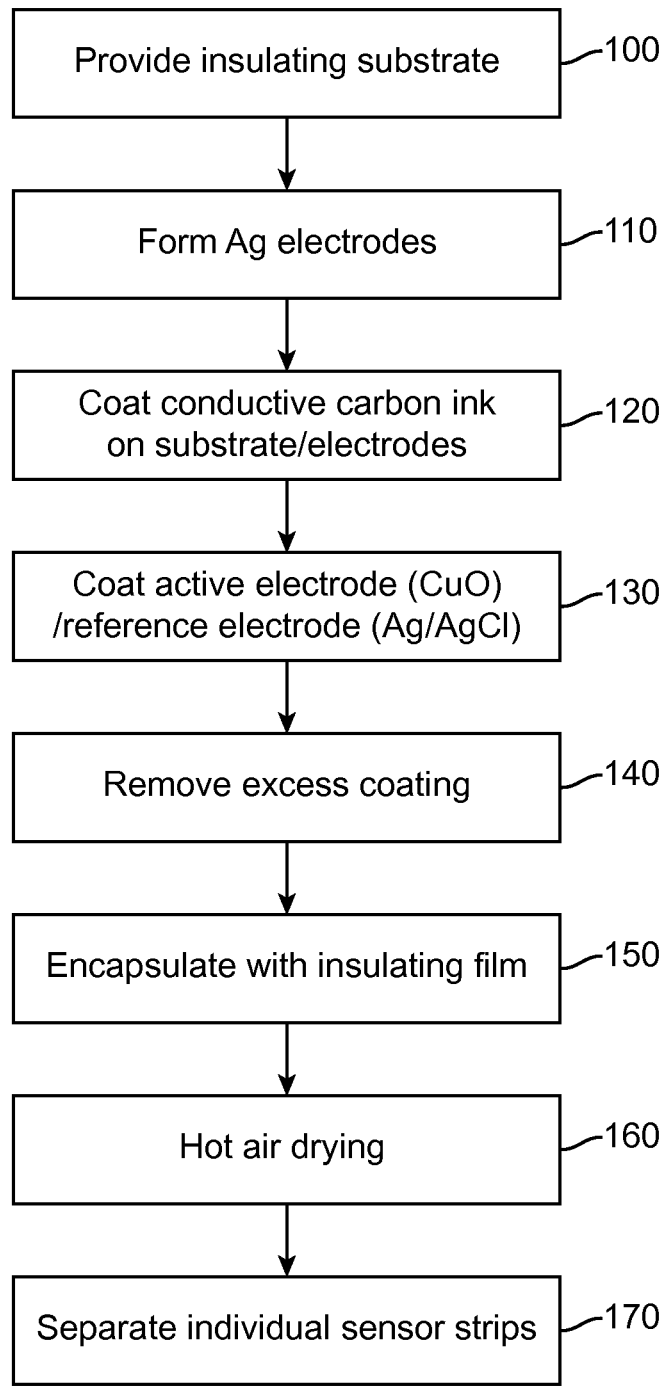
FIG. 2 illustrates a flow diagram of one embodiment of a fabrication method of a glucose sensor.

One embodiment of a fabrication method of the non-enzymatic glucose sensor is shown schematically in FIG. 2. Referring now to FIG. 2, the method comprises providing an insulating base/substrate at step 100. In various embodiments the insulating base/substrate 20 of FIG. 1 is made of polyvinylchloride (PVC), polyester (PE), polyether, polycarbonate, or the like. At step 110 one or more disposable silver electrodes 15 as shown in FIG. 1 are formed on the insulating base/substrate. At step 120, one or more conducting materials such as carbon ink are coated over the silver electrodes. In various embodiments, the conductive films are deposited on the substrate using screen printing, transfer printing, drop casting or any other technique known in the art. At step 130, active materials are deposited onto the electrodes. In one embodiment, active material coated on the reference electrode 13 is a mixture of Ag/AgCl. In one embodiment the active material for the active electrode 11 is a slurry of CuO nanostructures. Additionally, in one embodiment, step 130 includes forming the CuO starting from a solution of $CuSO_4$ containing a predetermined concentration of NaOH as explained further in detail. At step 140, excessive conductive materials and active materials are removed. At step 150, the electrodes are encapsulated with an insulating layer 21, in which sensing window 25 is provided. At step 160, the printed electrodes are then dried in a hot air oven at about 100° C. for one hour. In various embodiments, a single sensor or a bank of sensors is processed simultaneously. At step 170, after the electrodes are substantially dried, the substrate is parted to separate individual sensors 10. The individual sensors 10 are then incorporated into a flex circuit or suitable device electronics for testing the glucose level.

Figure 3:
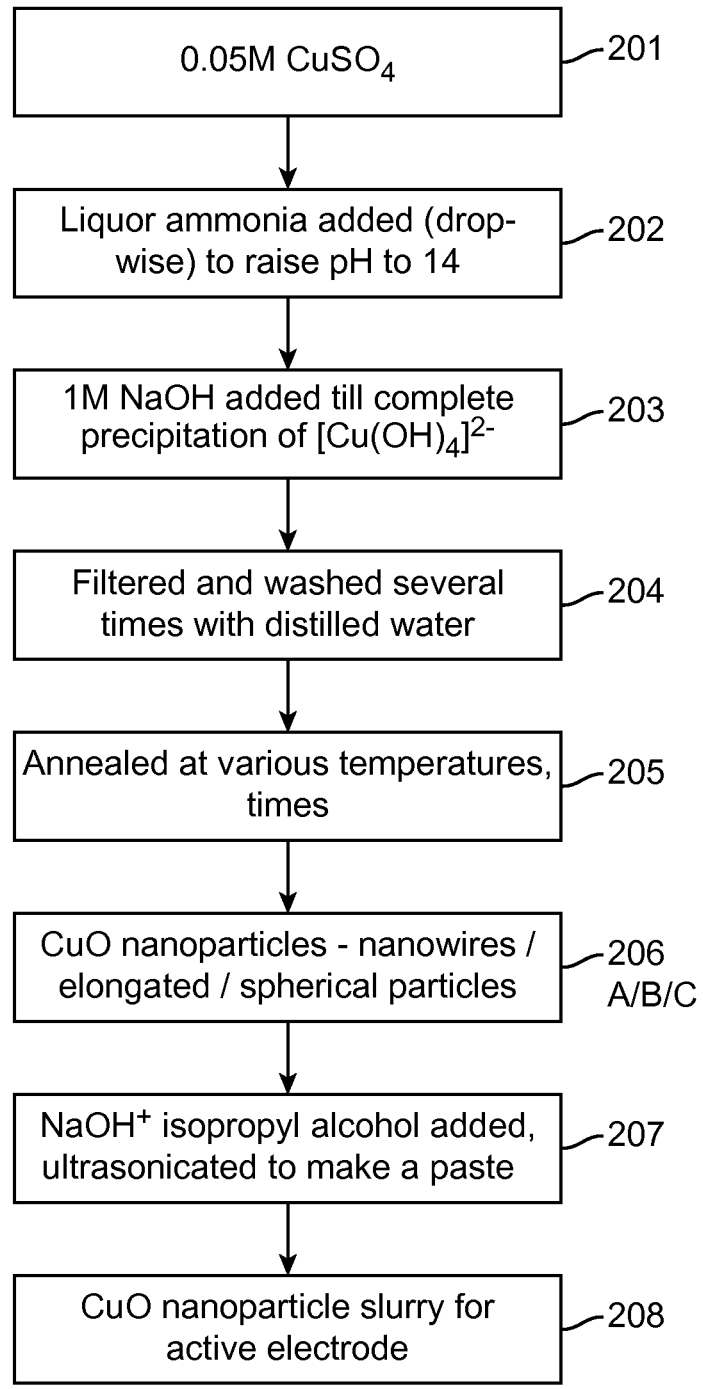
FIG. 3 is a flow diagram illustrating one embodiment of a method involved in producing CuO nanoparticles of the active electrodes of the invention.

In one embodiment, the CuO nanoparticles for the active electrode 11 of the sensors are prepared using a process as shown in FIG. 3. Specifically, the CuO nanoparticles may comprise spherical CuO nanoparticles, elongated nanoparticles or nanowires. The size of the nanoparticles preferably ranges from 5 nm-500 nm. According to FIG. 3, in step 201 0.5M $CuSO_4$ solution is used as starting material and in step 202 it is alkalized by addition of liquor ammonia drop-wise to raise the pH to 14. At this stage, in step 203, 1M NaOH is added drop-wise, until complete precipitation of copper hydroxide $[Cu(OH)_4]^{2-}$ takes place. In step 204, the precipitate is filtered and washed several times in distilled water. By annealing the copper hydroxide (step 205) at various temperatures, different morphologies of the CuO nanoparticles are obtained. In one embodiment of the invention, at step 205 the copper hydroxide is annealed at 180° C. for about three hours to obtain nanowires of CuO 206A. In a second embodiment, at step 205 elongated CuO nanoparticles 206B are obtained by thermal annealing of copper hydroxide complex at 400° C. for about three hours. In a third embodiment, at step 205 the copper hydroxide is annealed above 400° C., and more preferably at 450-500° C. for 3 hours to obtain spherical nanoparticles of CuO 206C. In step 207, the various CuO nanoparticles morphologies obtained are sonicated in a mixture of NaOH and isopropyl alcohol in various proportions, to obtain a homogeneous slurry 208. The nanoparticle slurry as prepared above is used to coat the active electrode 11 using various processes as explained earlier in relation to FIG. 2.

In one embodiment of the invention, one or more electrodes of the sensor are connected to a glucometer (not shown) which senses the glucose level in blood. In various embodiments the non-enzymatic glucose sensors of the invention are stable at a wider range of temperature and humidity than enzymatic sensors, with a high degree of selectivity and sensitivity. Copper and/or CuO modified electrodes catalyze the electro-oxidation of glucose in preference to other bio-molecules. Copper and CuO modified electrodes form a Cu(III) intermediate which catalyzes the oxidation of glucose. CuO modified electrodes have better catalytic activity than the copper modified electrodes, since in CuO modified electrodes, the formation of Cu(III) intermediate species is predominant.

The glucose sensing system allows the patient/clinician to have a high level of confidence in the effectiveness of their test strips over a longer period of time at a wider range of environmental conditions and thus greater confidence in the accuracy of the test results.

In one embodiment, the insulating base plate or substrate can be made of a variety of materials such as polymer, plastics, and ceramics. Materials may be chosen according to the requirement and application of electrode. For example, soft material should be chosen for invasive type sensors to reduce pain and avoid hurting tissue. For such sensors, insulating polymer materials such as polycarbonate, polyester, polyethylene terephthalate (PET), polyvinylchloride (PVC), polyether, polyamide, polyurethane, polyamide, etc., can be adapted. On the other hand, rigid materials which are not easy to be ruptured or bent, such as ceramics including silica or aluminium dioxide, can be adopted to provide robustness for external or in vitro use.

Additionally and optionally, the glucose sensors may be tested with glucose solutions of known concentrations. For example, electrochemical techniques such as amperometry may be used to determine a response current proportional to an analyte in a solution. The amperometric measurements disclosed using various embodiments of the invention can be performed using suitable instruments and readout electronics well known in the art such as an electrochemical work station. Alternatively, the measurements could be done using a dedicated measurement system configured to connect with disposable sensor strips that are inserted into the measurement system. The measurement system could incorporate digital electronics including a processor, a display and a memory for measurement, calibration, error correction, recording and display of the output of the sensor. Additionally, the measurement system could include wired and wireless communication systems such as USB (universal serial bus) or Bluetooth or infrared for transfer of data from the memory to a computer or a mobile phone or the internet.

The following examples illustrate one embodiment of preparing a non-enzymatic glucose sensor and of demonstrating the amperometric response of the prepared sensor. The examples should not be construed as limiting.

EXAMPLE 1

An exemplary device according to the various embodiments of the invention illustrated in FIGS. 1 to 3 was prepared. Three Ag electrodes 15 were deposited on a polyester film substrate as in FIG. 1. Conductive carbon ink was deposited over the electrodes by screen printing. Ag/AgCl paste was coated over the reference electrode 13. The active electrode 11 was coated with CuO slurry using drop casting, while the counter electrode was left as-coated with the carbon ink. CuO slurry was prepared using the process as detailed in FIG. 3. In step 206B, elongated nanoparticles of CuO by annealing the copper hydroxide complex obtained at step 204 at 400° C. for about three hours. To coat the active electrode 11, mg of the CuO was dispersed in 500 µl of 0.5M NaOH and 500 µl isopropyl alcohol in a 1:1 ratio, by ultrasonication for nearly 30 minutes.

The amperometric response of the non-enzymatic glucose sensor prepared as disclosed in Example 1 was compared with that of conventional glucose oxidase sensor. The disposable glucose sensing strip of the non-enzymatic sensor and one strip of the conventional glucose oxidase sensor were each exposed to 0.01 ml of the analyte containing ~10 mM of glucose solution. The amperometric response of the two sensors was measured using an electrochemical workstation. The maximum current generated by the current non-enzymatic sensor was in the few mA range, i.e. about 20 times that of the conventional glucose oxidase based sensor. This value is also at least two orders of magnitude greater than other non-enzymatic sensors such as those using mixed oxides (WO2012018777) or using $Cu_2O$ (Zhang et al.). The inventive sensor took about 900 ms to obtain the maximum response current of about 7 mA while the conventional sensor took about 800 ms to obtain maximum response current of about 0.35 mA.

EXAMPLE 2

Figure 4:
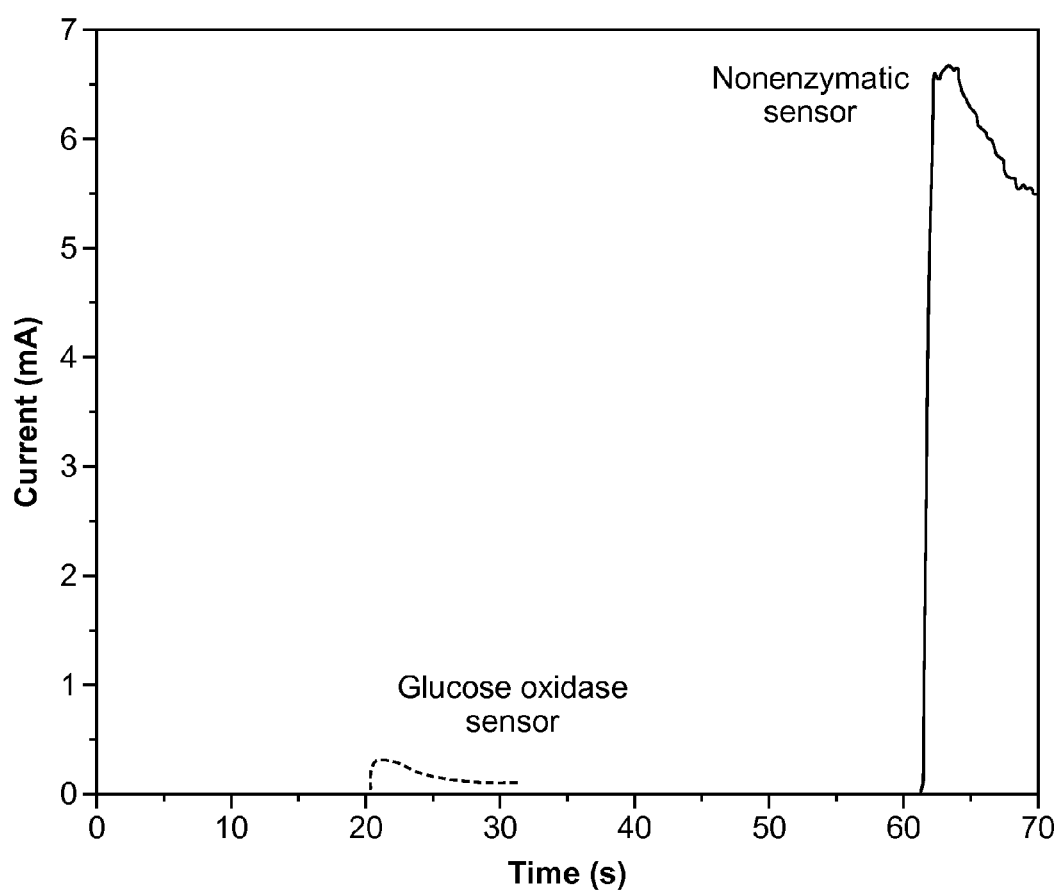
FIG. 4 shows the amperometric response of one embodiment of a non-enzymatic glucose sensor along with that of conventional glucose oxidase sensor.
Figure 5B:
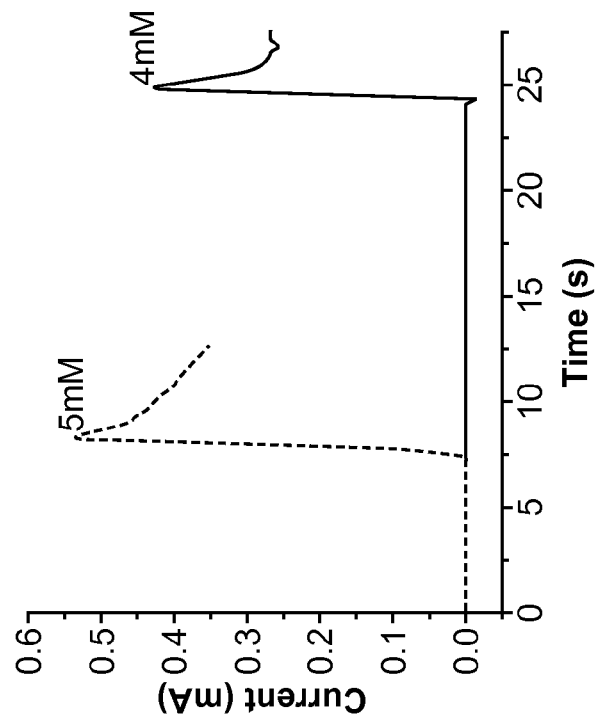
FIG. 5A to 5D show amperometric response of the non-enzymatic glucose sensor to various concentrations of glucose.
Figure 5A:
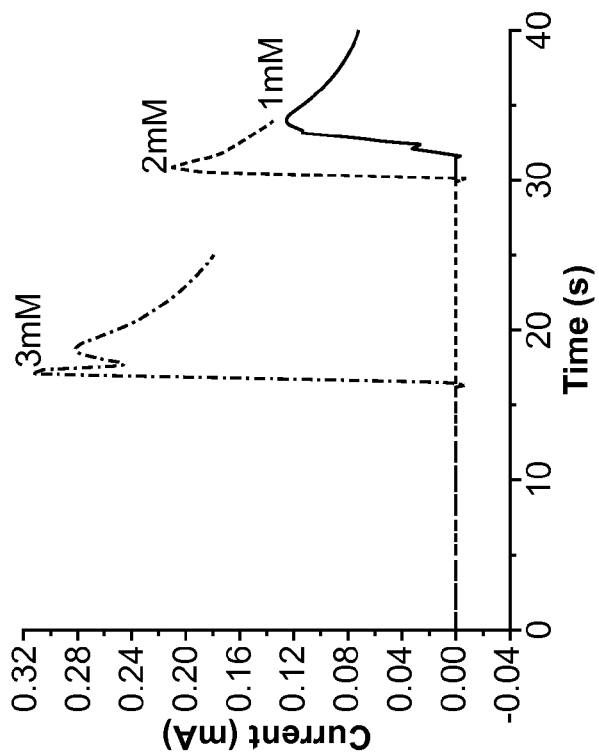
Figure 5D:
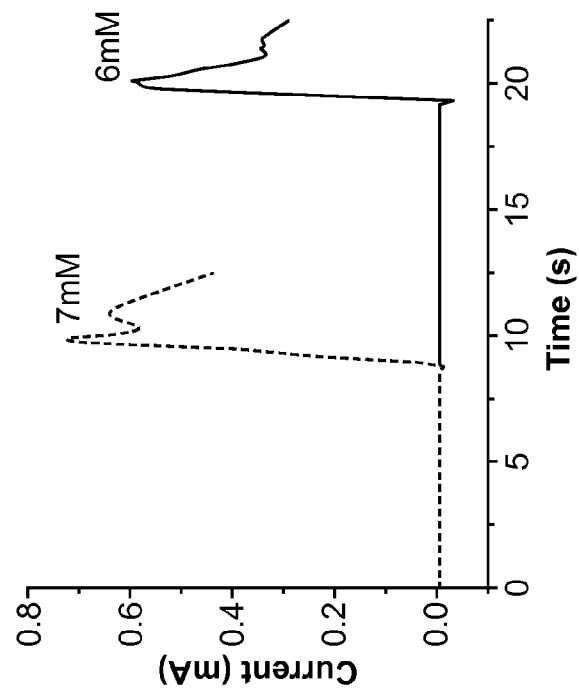
Figure 5C:
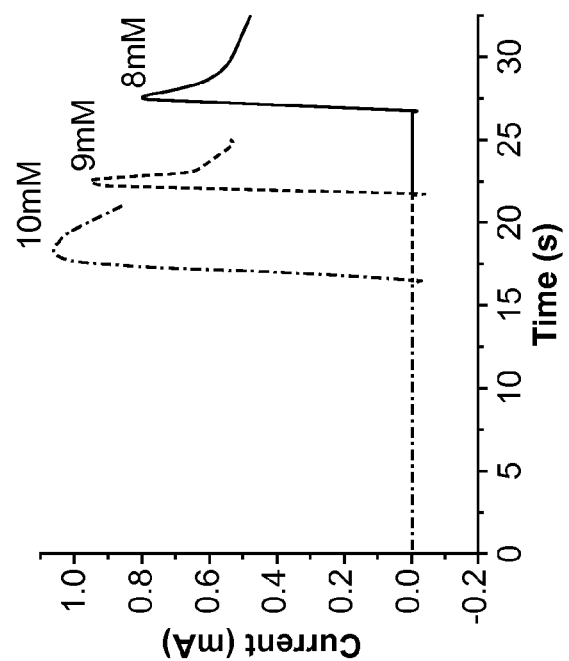
Figure 6:
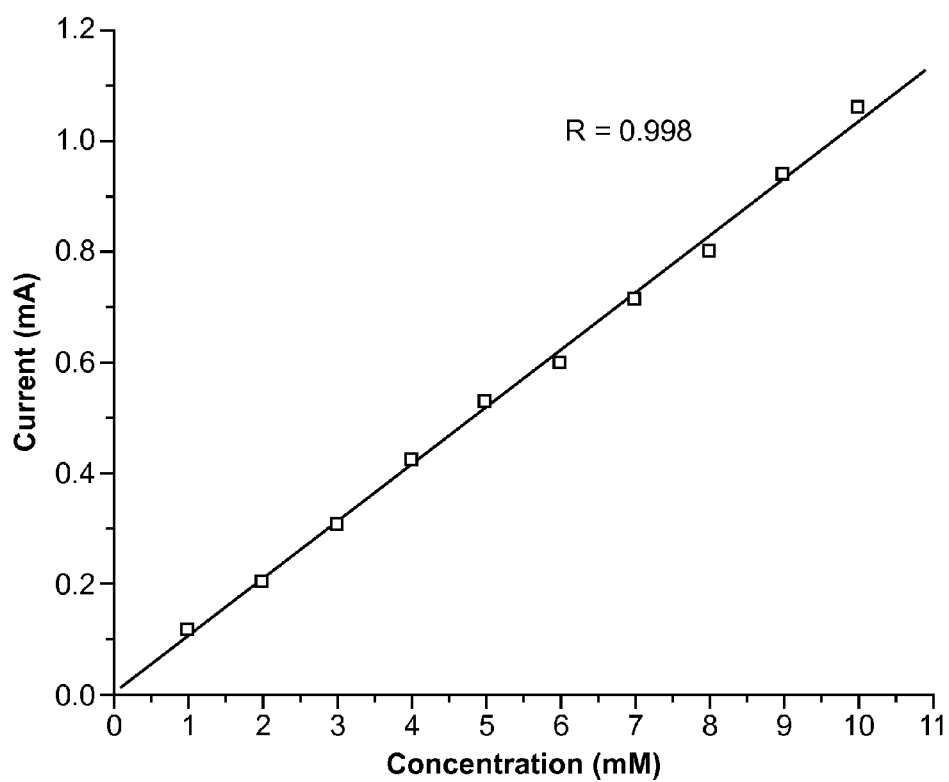
FIG. 6 is a calibration curve generated for amperometric response of the CuO sensor to glucose concentrations in the range 1 to 10 mM using the data in FIG. 5A to 5D.

A smaller version of the non-enzymatic sensor (compared to that used for FIG. 4) was prepared and the amperometric response calibrated for various glucose concentrations in the range 1 mM to 10 mM. The results of the calibration test are shown in FIG. 5A to 5D. The curves in FIG. 5A to 5D are plots of the sensor's response to solutions of the labeled concentrations with time on the X axis and current on the Y axis. The sensor responded in a few milliseconds after the glucose was injected and rose to peak values in each case as shown in FIG. 5A to 5D. The linearity of calibration of the sensor using the data in FIG. 5A to 5D is illustrated in FIG. 6.

Figure 7:
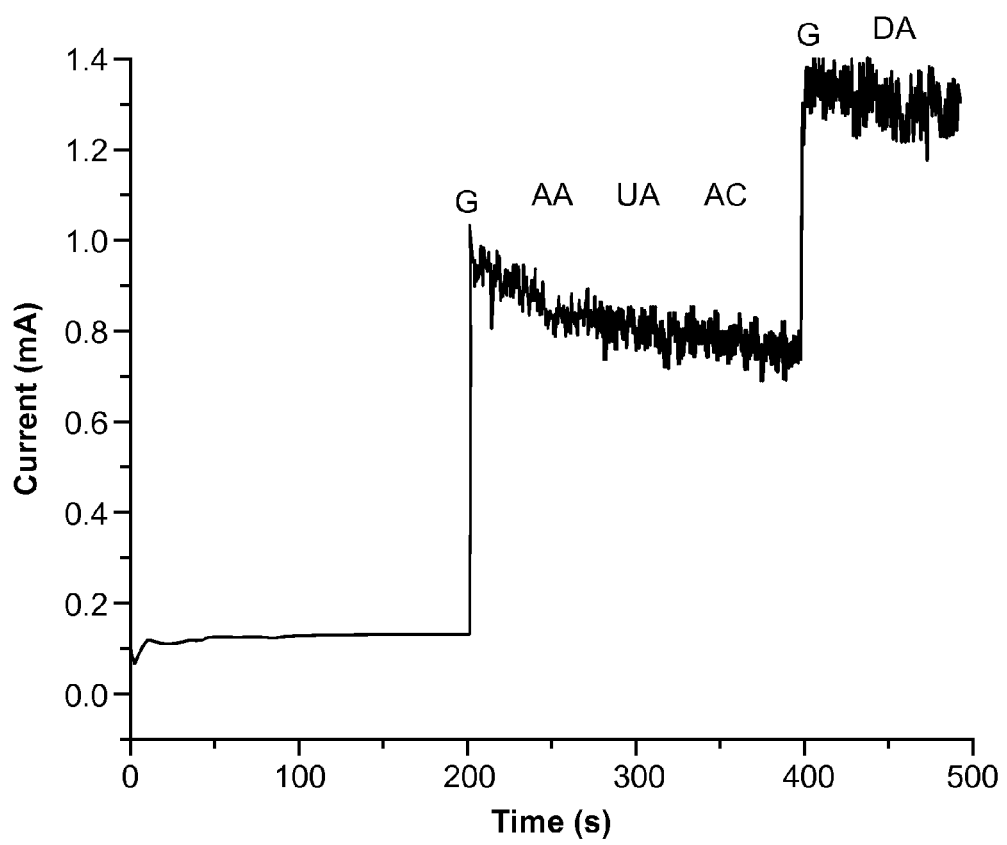
FIG. 7 illustrates amperometric response of the CuO sensor to glucose in the presence of other interfering molecules.

Response of the non-enzymatic glucose sensor to the presence of other common physiologically present interferents such as ascorbic acid (AA), uric acid (UA), acetaminophen (AC) and dopamine (DA) was tested. The sensor was exposed to about 10 mM of glucose, followed at intervals by the interferents AA, UA, AC and DA injections to the sensor and the data are shown in FIG. 7. The addition of interferents was done, in each case, at a concentration in which they are usually present in normal physiological fluids. The interferent exposure data show that the sensor is virtually immune to interference from the common species.

The results in Examples 1 and 2 show that the sensitivity of the non-enzymatic sensor is therefore, about 3-20 times greater than that of the conventional glucose oxidase based sensor, with comparable response times, thus achieving high degree of sensitivity. Being composed of inorganic constituents, the sensor is configured to provide stable performance at a wide range of temperature/humidity levels, including prolonged storage under those conditions.

The present embodiments are useful in connection with a device that is used to measure or monitor glucose level in an analyte. It is further contemplated that the sensor may also be used in connection with a device that is used to measure or monitor another analyte, including oxygen, carbon dioxide, proteins, drugs, or any combination thereof, found in bodily fluids, including subcutaneous fluid, dermal fluid (sweat, tears, and the like), interstitial fluid, or other bodily fluid of interest, for example, or any combination thereof.

Various embodiments as described above may be used in a continuous analyte monitoring system that includes at least one analyte sensor to be used in continuous and/or automatic in vivo monitoring of the level of one or more analytes. In such embodiment, the monitoring device and system may include a sensor, at least a portion of which is positionable beneath the skin of the user for in vivo detection of an analyte, including glucose, lactate, and the like, in a body fluid. The sensor may be, for example, subcutaneously positionable in a patient for the continuous or periodic monitoring of a level of an analyte in a patient's interstitial fluid. The sensor response may be correlated and/or converted to analyte levels in blood or other fluids. In one embodiment, a sensor may be positioned in contact with interstitial fluid to detect the level of glucose in patient's bloodstream. In another embodiment, the sensor may be insertable into a vein, artery, or other portion of the body containing a fluid. Embodiments of the sensor may be configured for monitoring the level of the analyte over a time period which may range from seconds, minutes, hours, days, weeks to months, or longer. Alarms may notify the user with the monitored analyte levels that may be of concern, in advance of the user's analyte level reaching a predetermined level. This provides the user with an opportunity to take corrective action. In another embodiment, discrete monitoring of one or more analytes may be accomplished through using the sensor in vitro. One or more sensors that include various nanomaterials may be configured as either in vivo or in vitro sensors.

Also provided herein are kits for use in practicing the subject systems, devices, and methods, where the kits typically include one or more of the above sensors, as described above, along with a dedicated measurement system including processor, memory and a display.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate. While the above is a complete description of the preferred embodiments of the invention, various alternatives, modifications, and equivalents may be used. Therefore, the above description should not be taken as limiting the scope of the invention which is defined by the appended claims.

What is claimed is:

1. A device for detecting glucose, comprising:
   at least one active electrode configured to catalyze the electro-oxidation of glucose in preference to other bio-molecules;
   wherein the active electrode consists essentially of
      a slurry coating of CuO nanoparticles and NaOH; a coating of conductive carbon; and a coating of silver; and
      wherein the active electrode is encapsulated in an insulating film layer in which a sensing window is provided and wherein the device is configured to produce linear response currents of 0.3 to 1 mA when exposed to glucose concentrations in the 3-10 mM range.

2. The device of claim 1, wherein the CuO nanoparticles comprise spherical, CuO nanoparticles.

3. The device of claim 1, wherein the size of the nanoparticles ranges from 5nm to 500 nm.

4. The device of claim 1, wherein the device is further configured to produce linear response currents of 0.1 to 0.3 mA when exposed to glucose concentrations in the 1-3 mM range.

* * * * *